United States Patent [19]

Allen, Jr.

[11] Patent Number: 4,655,747
[45] Date of Patent: Apr. 7, 1987

[54] DUAL CHAMBERED SYRINGE

[76] Inventor: Robert E. Allen, Jr., 2041 Buckingham Ct., Decatur, Ga. 30035

[21] Appl. No.: 824,125

[22] Filed: Jan. 30, 1986

[51] Int. Cl.⁴ ............................................. A61M 37/00
[52] U.S. Cl. ........................................ 604/89; 604/191
[58] Field of Search ................. 604/191, 89, 91, 92, 604/248, 187

[56] References Cited

U.S. PATENT DOCUMENTS

| | | | |
|---|---|---|---|
| 553,234 | 1/1896 | Finot | 604/191 |
| 984,037 | 2/1911 | Sheets | 604/191 |
| 3,749,084 | 7/1973 | Cucchiara | 604/191 |

Primary Examiner—John D. Yasko
Attorney, Agent, or Firm—James B. Middleton

[57] ABSTRACT

A dual chambered syringe of the type having concentric barrels. The inner barrel can be formed of a generally conventional syringe, and the outer barrel is formed of a modified conventional syringe. A sealing ring of resilient rubber spaces the two barrels apart and forms a liquid seal between the two barrels. A passageway through the sealing ring is alignable with a hole in the inner barrel to allow communication between the two chambers. A rear plate is fixed to the inner barrel and rotatable on the outer barrel so the two barrels can be rotated to align the hole with the passageway when desired.

7 Claims, 4 Drawing Figures

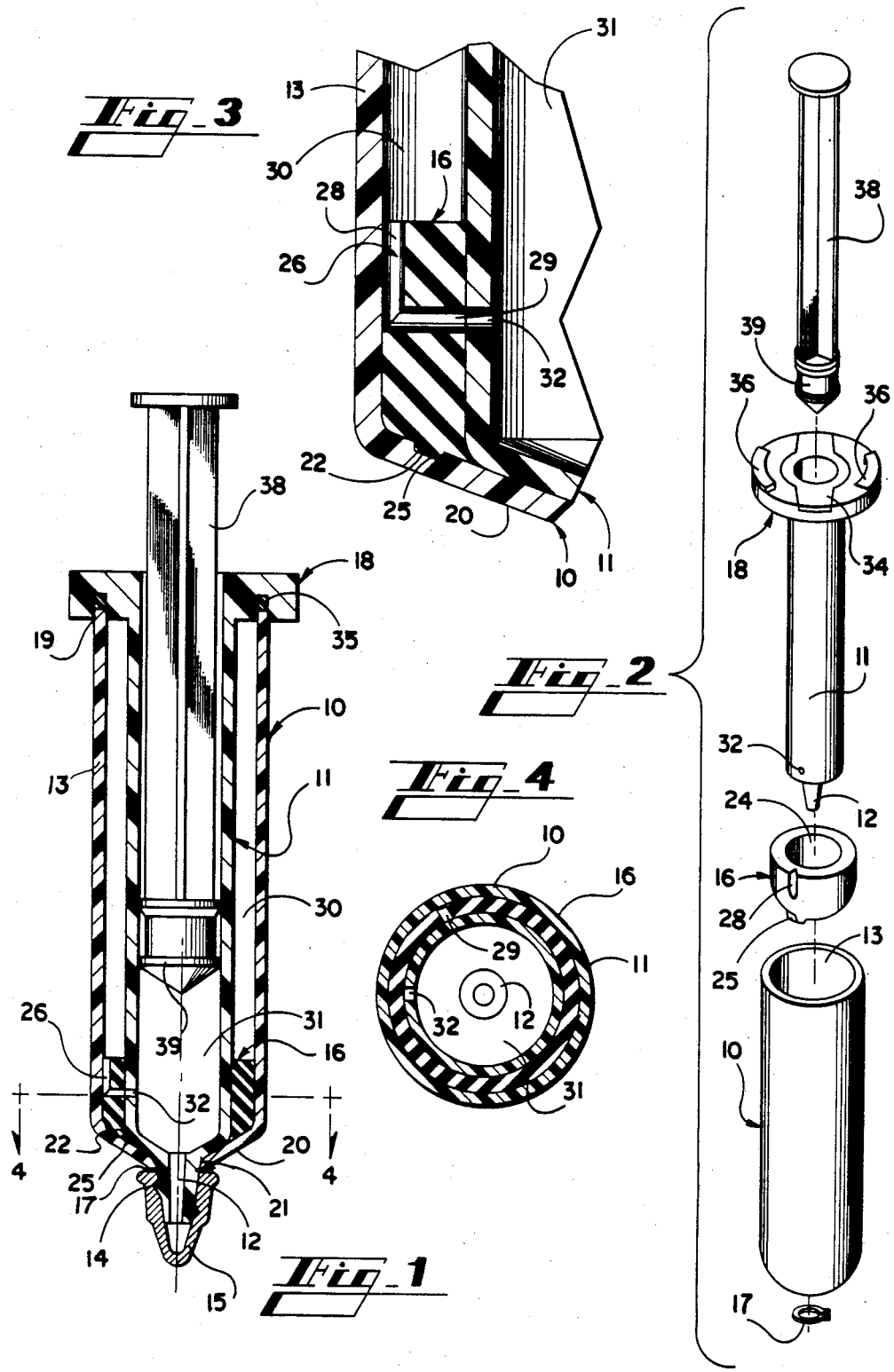

DUAL CHAMBERED SYRINGE

INFORMATION DISCLOSURE STATEMENT

There have been numerous efforts in the prior art to provide a syringe having facility for containing a plurality of liquids at one time. The syringes have taken various forms, including the provision of two syringe barrels in side-by-side relationship, as well as various concentrically arranged dual barrels. U.S. Pat. No. 553,234 issued to Finot discloses a syringe having concentrically arranged barrels and a single plunger, the barrels being partially rotatable with respect to each other selectively to connect the inner and outer barrel with the tip of the syringe. The arrangement disclosed in the patent to Finot would be difficult to construct; and, the arrangement is so remote from present day syringes that currently standard parts could not be utilized to manufacture the device.

The patent to Allen, U.S. Pat. No. 3,872,864, discloses a similar arrangement in that there are two concentric barrels for the syringe, and one plunger. Rather than the arrangement disclosed in the patent to Finot, the patent to Allen provides means for filling the central chamber through the tip of the syringe, separate means for filling the outer chamber of the syringe, and means for connecting the two chambers for allowing the liquid in the outer chamber to be drawn into the inner chamber. This arrangement is extremely difficult to manufacture, especially considering the necessity for appropriate sealing of the selective connection between chambers.

SUMMARY OF THE INVENTION

This invention relates generally to dual chambered syringes, and is more particularly concerned with a dual chambered syringe and means for constructing the syringe using existing components.

The present invention provides a dual chambered syringe having a single plunger, the two chambers of the syringe being selectively connectible for transferring a liquid from one chamber to the other. The syringe of the present invention is so constructed that two generally conventional syringes can be modified and assembled, with a minimum of additional parts, to provide the dual chambered syringe of the present invention. A larger syringe without a protruding tip receives a sealing ring, and the sealing ring receives a smaller syringe therethrough. A rear plate connects the rear ends of the two syringes together, thereby defining concentric cylindrical chambers. The sealing ring includes passage means; and, and opening in the inner syringe is selectively alignable with the passage means for causing the inner and outer chambers to be in communication.

BRIEF DESCRIPTION OF THE DRAWINGS

These and other features and advantages of the present invention will become apparent from consideration of the following specification, when taken in conjunction with the accmpanying drawings, in which:

FIG. 1 is a longitudinal cross-sectional view showing a dual chambered syringe made in acordance with the present invention;

FIG. 2 is an exploded perspective view showing the syringe of FIG. 1;

FIG. 3 is an enlarged, fragmentary cross-sectional view showing the construction of the sealing ring; and, FIG. 4 is an enlarged cross-sectional view taken substantially along the line 4—4 in FIG. 1.

DETAILED DESCRIPTION OF THE EMBODIMENT

Referring now more particularly to the drawings, and to that embodiment of the invention here presented by way of illustration, FIG. 1 discloses a dual chambered syringe having an outer barrel 10 and an inner barrel 11. A protruding tip 12 includes a locking flange 14 for receiving a cap 15, or a hypodermic needle, biopsy needle, or other apparatus with which the syringe may be used. Those skilled in the art will understand that the locking flange 14 is of a generally standard type in the medical industry, and the various needles and the like will be readily received on the tip 12 and locked in place using the flange 14.

As is discussed below, the outer barrel 10 and inner barrel 11 may be formed of two conventional syringes, the tip 12 being on the inner syringe. Thus, to hold the two syringes together, a locking ring 17 can engage the tip 12 and prevent removal of the tip 12 from the opening in the outer syringe 10. It will of course be understood by those skilled in the art that the syringes 10 and 11 can be fixed together by other means such as gluing, welding or the like.

Between the outer barrel 10 and inner barrel 11, there is a sealing ring 16 arranged to seal the outer barrel 10 with respect to the inner barrel 11. At the rear of the syringe, there is a rear plate 18 here shown as integrally formed with the inner barrel 11, with the outer barrel 10 received in an appropriate groove 19. This will be discussed in more detail hereinafter.

Looking now at FIG. 2 of the drawings, it will be seen that the outer barrel 10 may be formed as a generally conventional syringe, but without the rear flanges and forward tip. Thus, the outer barrel 10 may be formed by slightly modifying a mold for a conventional syringe, or by cutting off the forward tip and rear flanges of syringes already molded. In either event, looking at FIGS. 1 and 2 of the drawings, it will be realized that the outer barrel 10 comprises a generally cylindrical wall member 13, and a sloped bottom wall 20 with a central opening 21. The inner surface of the bottom wall 20 is provided with an indentation 22.

The sealing ring 16 will preferably be formed of a resilient rubber material such as Neoprene or the like. The sealing ring 16 is generally annular, having an outside diameter to fit snugly against the inside of the wall 13 of the outer barrel 10 to form a tight seal therewith. The central opening 24 in the sealing ring 16 has a diameter such as to fit snugly around the outside of the inner barrel 11 to form a tight seal therewith.

Looking at FIG. 3 in conjunction with FIG. 2, it will be seen that the sealing ring 16 has a protrusion 25 sized to be received within the depression 22 in the bottom wall 20 of the outer barrel 10. While it is contemplated that the sealing ring 16 may be adhesively fixed to the outer barrel 10, use of the protrusion 25 and depression 22 may obviate the need for adhesives or the like, and will provide additional security against rotation even when an adhesive is utilized.

Since the two chambers of the syringe must communicate when desired, the sealing ring 16 is provided with a passageway 26. It will be seen that the passageway 26 includes a longitudinally extending groove 28 communicating with a radially extending opening 29. The groove 28, with the wall of the outer barrel 10, forms an opening extending from the outer chamber 30 to the radially extending opening 29; and, the radially extending opening 29 extends inwardly to communicate with the inner chamber 31. It will be noted however that the inner chamber 31 may communicate with the radially extending opening 29 only through the hole 32 in the wall of the inner barrel 11. Thus, with attention to FIG. 4 of the drawings, it will be seen that there is only one rotational position of the inner barrel 11 that will allow communication between the inner chamber 31 and the outer chamber 30. When the hole 32 in the wall of the inner barrel 11 is aligned with the radially extending opening 29 in the sealing ring 16, the inner and outer chambers 31 and 30 are in communication. At all other positions, the two chambers are isolated from each other, the sealing ring 16 adequately sealing the opening 32.

Looking again at FIGS. 1 and 2 of the drawings, it will be seen that the inner barrel 11 is a substantially conventional syringe with the exception of the opening 32, and the presence of the rear plate 18. As is shown in FIG. 2, the inner barrel 11 may be formed of a conventional syringe, even including the usual rear flanges 34.

In order to provide the rear plate 18, the inner barrel 10 may be appropriately mounted, and the plate 18 actually cast around the syringe, the flanges 34 of the syringe becoming simply a part of the rear plate 18. Alternatively, it will be obvious that the ring 18 may be separately molded, leaving an appropriate opening to receive the flanges 34. The two pieces can then be assembled using an appropriate adhesive, or utilizing sonic welding or the like.

It will be seen that the rear plate 18 will define a circular groove 19 for receiving the rear end of the wall 13 of the outer barrel 10. A seal such as an O-ring 35 can be used to assure the complete sealing of the rear end of the outer chamber 30.

As is illustrated in FIG. 2 of the drawings, it is also contemplated that flanges such as the flanges 36 may be molded with the rear plate 18. If the rear plate 18 is not to be permanently assembled with a conventional syringe as described above, the flanges 36 can be provided to receive the conventional flanges 34 on a syringe. Final hand assembly can then be made to produce the dual chambered syringe.

Finally, it will be seen that a conventional plunger 38 is received within the inner chamber 31. The plunger 38 is conventional in the art, and inlcudes a piston 39 at its lower, or inner, end. The piston 39 is conventionally made of a resilient rubber material that will slidably seal against the inside of the barrel 11.

From the foregoing description, operation of the device should now be understandable. With the inner barrel 11 rotated so that the opening 32 is not aligned with the radially extending opening 29, the inner barrel 10 will act as a conventional syringe. A needle or the like can be received over the flange 14 on the tip 12. With the plunger 38 at the bottom of the inner barrel 11, the needle can be placed into one fluid, the plunger 38 withdrawn, and the inner chamber 31 will receive a quantity of the fluid. At this point, the rear plate 18 can be rotated with respect to the outer barrel 10, causing the entire inner barrel 11 to rotate to align the opening 32 in the inner barrel 11 with the radially extending opening 29 in the sealing ring 16.

With this alignment, a valve can be closed, or a cap 15 placed over the tip 12; then, the plunger 38 can be depressed, causing fluid within the inner chamber 31 to pass through the passageway 26 and enter the outer chamber 30. Once the fluid is transferred to the outer chamber 30, the parts can again be rotated to seal the outer chamber with respect to the inner chamber, and another sample can be drawn into the inner chamber.

The foregoing description is only one example of a use of the dual chambered syringe of the present invention. It will also be understood that the syringe can be prepackaged with a dry material in the outer chamber 30 and a liquid in the inner chamber 31. When the two are to be mixed, the liquid can be transferred from the inner chamber to the outer chamber by capping the tip 12 as is shown in FIG. 1 of the drawings, aligning the opening 32 with the passageway 26, and pressing the plunger 38. If the resulting mixture is then to be injected or otherwise dispensed, the plunger can be pulled back, causing the now-dissolved material to pass through the passageway 26 and into the inner chamber 31. Once the mateial is within the inner chamber 31, the inner barrel 11 can be rotated, the cap 15 removed and a needle or the like locked onto the tip 12, and the material can be dispensed as desired.

It will therefore be understood by those skilled in the art that the embodiment here presented is by way of illustration only, and is meant to be in no way restrictive; therefore, numerous changes and modifications may be made, and the full use of equivalents resorted to, without departing from the spirit or scope of the invention as outlined in the appended claims.

What is claimed is:

1. A dual chambered syringe comprising an inner barrel defining an inner chamber therein, an outer barrel concentric with said inner barrel and defining an outer chamber between said inner barrel and said outer barrel, a sealing ring at one end of said syringe disposed within said outer chamber and sealing said outer barrel with respect to said inner barrel, a rear plate connecting the opposite end of said outer barrel and said inner barrel, and a plunger received within said inner chamber, said sealing ring defining passage means therein for selectively allowing communication between said outer chamber and said inner chamber, said inner barrel defining a hole therethrough selectively alignable with said passage means, said outer barrel and said inner barrel being selectively rotatable with respect to each other for aligning said hole in said inner barrel with said passage means in said sealing ring, said passage means in said sealing ring including a radially extending opening through said sealing ring, a groove extending longitudinally of said sealing ring from said radially extending opening, the arrangement being such that said groove connects said outer chamber with said radially extending opening and said radially extending opening selectively connects said groove with said hole in said inner barrel.

2. A dual chambered syringe as claimed in claim 1, said rear plate being fixed to said inner barrel, said rear plate defining a groove therein for rotatably receiving said opposite end of said outer barrel, the arrangement being such that said rear plate can be rotated to rotate said inner barrel with respect to said outer barrel.

3. A dual chambered syringe as claimed in claim 2, said inner barrel incuding flanges extending radially from said opposite end of said inner barrel, said flanges being fixed to said rear plate.

4. A dual chambered syringe as claimed in claim 3, said outer barrel further including a bottom wall defining a central opening therein, said inner barrel including a tip extending through said central opening in said bottom wall, said sealing ring covering said bottom wall and sealing said inner barrel with respect to said outer barrel.

5. A dual chambered syringe as claimed in claim 4, said bottom wall defining a depression therein, said sealing ring including a protrusion formed integrally therewith and sized and located to be received within said depression, the arrangement being such that protrusion locks said sealing ring to said bottom wall to prevent relative rotation therebetween.

6. A dual chambered syringe, comprising an inner barrel defining an inner chamber therein, an outer barrel concentric with said inner barrel and defining an outer chamber between said inner barrel and said outer barrel, a sealing ring at one end of said syringe disposed within said outer chamber and sealing said outer barrel with respect to said inner barrel, a rear plate connecting the opposite end of said outer barrel and said inner barrel, and a plunger received within said inner chamber, said sealing ring defining passage means therein for selectively allowing communication between said outer chamber and said inner chamber, said inner barrel defining a hole therethrough selectively alignable with said passage means, said outer barrel and said inner barrel being selectively rotatable with respect to each other for aligning said hole in said inner barrel with said passage means in said sealing ring, said outer barrel further including a bottom wall defining a central opening therein, said inner barrel including a tip extending through said central opening in said bottom wall, said sealing ring covering said bottom wall and sealing said inner barrel with respect to said outer barrel.

7. A dual chambered syringe comprising an inner barrel defining an inner chamber therein, an outer barrel concentric with said inner barrel and defining an outer chamber between said inner barrel and said outer barrel, a sealing ring at one end of said syringe disposed within said outer chamber and sealing said outer barrel with respect to said inner barrel, a rear plate connecting the opposite end of said outer barrel and said inner barrel, and a plunger received within said inner chamber, said sealing ring defining passage means therein for selectively allowing communication between said outer chamber and said inner chamber, said inner barrel defining a hole therethrough selectively alignable with said passage means, said outer barrel and said inner barrel being selectively rotatable with respect to each other for aligning said hole in said inner barrel with said passage means in said sealing ring, said outer barrel further including a bottom wall defining a central opening therein, said inner barrel including a tip extending through said central opening in said bottom wall, said sealing ring covering said bottom wall and sealing said inner barrel with respect to said outer barrel said bottom wall defining a depression therein, said sealing ring including a protrusion formed integrally therewith and sized and located to be received within said depression, the arrangement being such that said protrusion locks said sealing ring to said bottom wall to prevent relative rotation therebetween.

* * * * *